US006811664B2

(12) United States Patent
Lenfers et al.

(10) Patent No.: US 6,811,664 B2
(45) Date of Patent: Nov. 2, 2004

(54) ELECTROCHEMICAL SENSOR ELEMENT

(75) Inventors: Martin Lenfers, Aidlingen (DE);
Harry Braun, Heimsheim (DE);
Walter Strassner, Schorndorf (DE);
Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 74 days.

(21) Appl. No.: 10/016,787

(22) Filed: Oct. 26, 2001

(65) Prior Publication Data

US 2002/0166765 A1 Nov. 14, 2002

(30) Foreign Application Priority Data

Oct. 26, 2000 (DE) .......................................... 100 53 107

(51) Int. Cl.[7] .............................................. G01N 27/41
(52) U.S. Cl. ........................ 204/427; 204/425; 204/426
(58) Field of Search ................................. 204/421–429

(56) References Cited

U.S. PATENT DOCUMENTS

| 4,505,807 | A | * | 3/1985 | Yamada |  |
|---|---|---|---|---|---|
| 4,559,126 | A | * | 12/1985 | Mase et al. |  |
| 4,755,274 | A | * | 7/1988 | Mase et al. | 204/427 |
| 5,217,588 | A | * | 6/1993 | Wang et al. | 205/781 |
| 5,314,604 | A | * | 5/1994 | Friese et al. |  |
| 5,939,615 | A | * | 8/1999 | Kato et al. |  |
| 6,071,393 | A | * | 6/2000 | Oshima et al. | 204/425 |

* cited by examiner

Primary Examiner—Kaj K. Olsen
(74) Attorney, Agent, or Firm—Kenyon & Kenyon

(57) ABSTRACT

A sensor element for determining the concentration of a gas component in a gas mixture, particularly for determining the oxygen concentration in exhaust gases of internal combustion engines. The sensor element includes at least one pump cell, which has at least one first pump electrode located in a measuring gas chamber and at least one second pump electrode, located on a surface of the sensor element facing the gas mixture, as well as at least one concentration cell, which has at least one reference electrode located in a reference gas chamber and at least one measuring electrode, located in the measuring gas chamber, which cooperates with the reference electrode. The measuring gas chamber and the reference gas chamber are essentially located in the same layer level (plane) of the sensor element which has a layered construction. At least one barrier layer is provided which, at least to a large extent, prevents ionic conduction between at least one electrode of the pump cell and at least one electrode of the concentration cell.

9 Claims, 2 Drawing Sheets

ELECTROCHEMICAL SENSOR ELEMENT

FIELD OF THE INVENTION

The present invention relates to an electrochemical sensor element for determining the concentration of a gas component in a gas mixture, particularly for determining the oxygen concentration in exhaust gases of internal combustion engines.

BACKGROUND INFORMATION

An electrochemical sensor element of this type is described in, for example, German Patent No. 199 41 051. These types of sensor elements are used in gas measurement detectors known to those skilled in the art as broadband-lambda probes and are used for regulating the air/fuel ratio of combustion mixtures in motor vehicle engines. In these sensor elements, a concentration cell is combined with an electrochemical pump cell. The concentration cell has a measuring electrode located in a measuring gas chamber and a reference electrode located in a reference gas chamber and measures the oxygen partial pressure of the exhaust gas, which reaches the measuring gas chamber via a diffusion barrier, relative to the oxygen partial pressure of a reference gas in the reference gas chamber. The measuring gas chamber and the reference gas chamber are located in the same layer level of the sensor element.

The pump cell has a first pump electrode located in the measuring gas chamber and a second pump electrode located on a surface of the sensor element facing the exhaust gas and pumps oxygen ions from the exhaust gas into the measuring gas chamber or, conversely, from the measuring gas chamber into the exhaust gas. Through an external circuit element, the pump flow flowing through the pump cell is adjusted in such a way that a preset oxygen partial pressure is set in the measuring gas chamber. The oxygen partial pressure of the exhaust gas can be determined from the pump flow necessary for this purpose.

It is disadvantageous in the known sensor element that an undesired exchange of oxygen ions can occur between the electrodes of the pump cell and the electrodes of the concentration cell, which interferes with the intended function of the sensor. Thus, the oxygen partial pressure of the reference gas may be changed by the exchange of oxygen between the second pump electrode and the reference electrode. Since the concentration cell measures the ratio of the oxygen partial pressure in the measuring gas chamber and the oxygen partial pressure in the reference gas chamber, an incorrect oxygen partial pressure is set in the measuring gas chamber and therefore an incorrect value is determined for the oxygen partial pressure of the exhaust gas.

SUMMARY OF THE INVENTION

The electrochemical sensor element according to the present invention has the advantage relative to the related art that the exchange of ions of the gas component between the electrodes of the pump cell and the electrodes of the concentration cell is prevented by a barrier layer.

The barrier layer located between the reference electrode and the second pump electrode prevents the concentration of the gas component in the reference gas from being corrupted by the exchange of oxygen ions between the reference electrode and the pump electrode. The barrier layer is designed in such a way that the function of the concentration cell and the pump cell is not impaired. For this purpose, a cutout is provided in the region of the electrodes of the concentration cell and/or of the pump cell.

DETAILED DESCRIPTION

Figure 1:
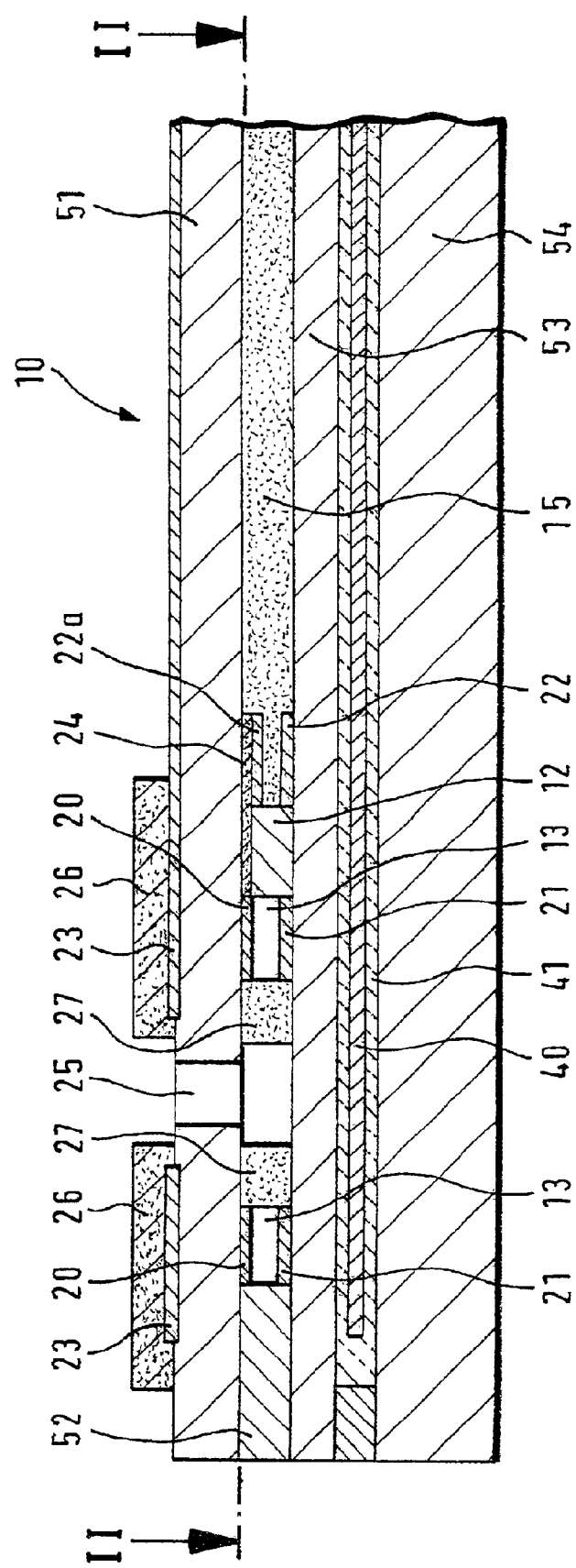
FIG. 1 shows a longitudinal section through an exemplary embodiment of a sensor element according to the present invention.
Figure 2:
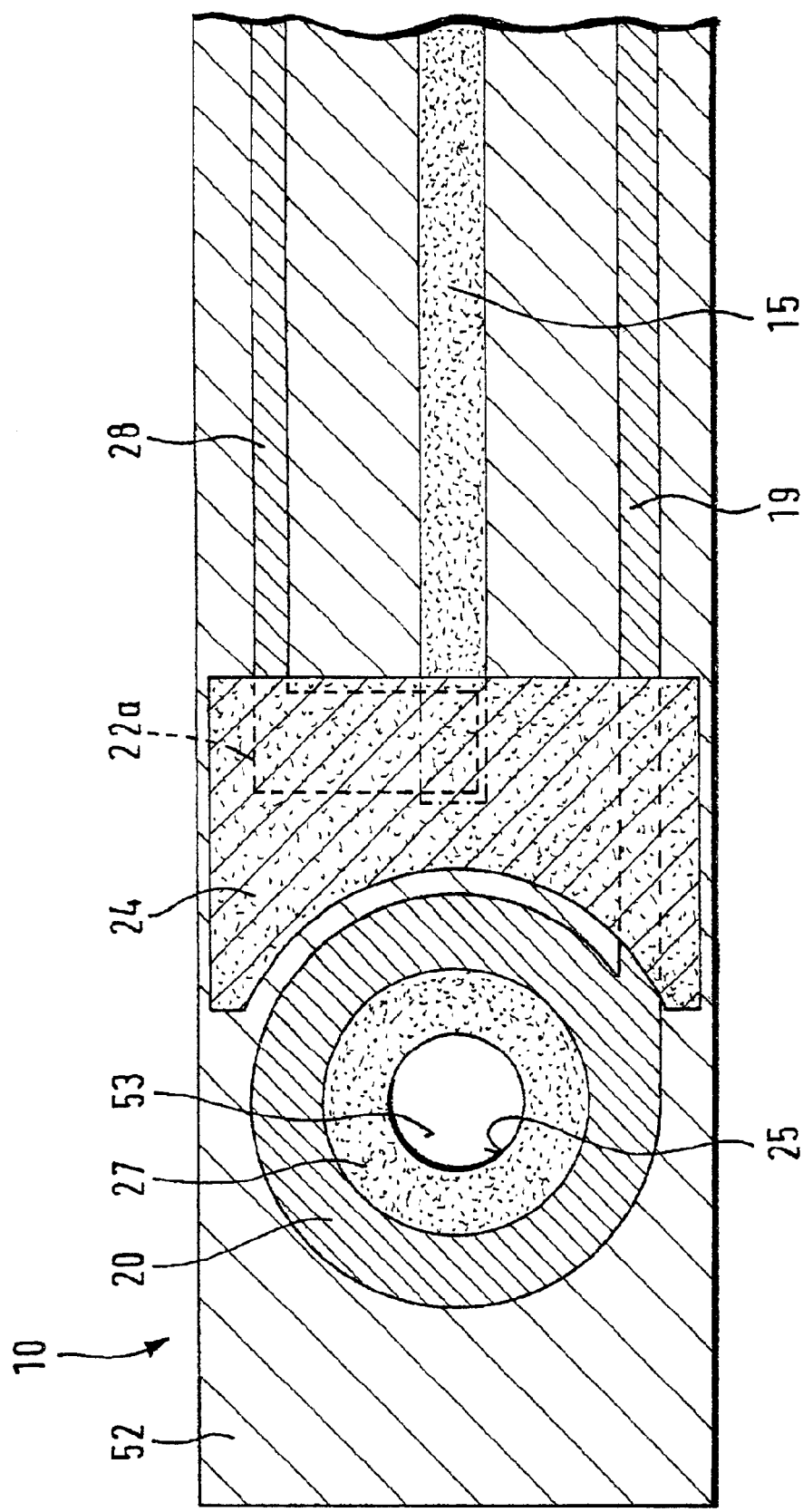
FIG. 2 shows a cross section of the exemplary embodiment along the sectional line II—II in FIG. 1.

FIG. 1 and FIG. 2 show a sensor element 10 of a broadband-lambda probe as an exemplary embodiment of the present invention, which is designed as a layered system and in which a reference gas chamber 15 and a measuring gas chamber 13 are located in the same layer level of sensor element 10. Sensor element 10 has a first, second, third, and fourth solid electrolyte layer 51, 52, 53, 54. A gas access hole 25 is introduced in first solid electrolyte layer 51 and second solid electrolyte layer 52. Second solid electrolyte layer 52 includes reference gas chamber 15 and measuring gas chamber 13, as well as a diffusion barrier 27 located between gas access hole 25 and measuring gas chamber 13. Measuring gas chamber 13 and reference gas chamber 15 are separated gas-tight by a partition wall 12, which forms a section of second solid electrolyte layer 52. The gas mixture can reach measuring gas chamber 13 via gas access hole 25 and diffusion barrier 27. Reference gas chamber 15 is connected to the surrounding air and is made of a porous material. A heater 40, embedded in a heater insulation 41, is provided between third solid electrolyte layer 53 and fourth solid electrolyte layer 54.

A first, ring-shaped pump electrode 20 having a supply lead 19 is located on first solid electrolyte layer 51 in measuring gas chamber 13. First pump electrode 20, together with a second pump electrode 23, also ring-shaped, which is also located on first solid electrode layer 51 on the side opposite first pump electrode 20, forms a pump cell. Second pump electrode 23 is covered by a porous layer 26. A ring-shaped measuring electrode 21 in measuring gas chamber 13 and a reference electrode 22 in reference gas chamber 15 are located on third solid electrolyte layer 53. A further reference electrode 22a having a supply lead 28 is provided on first solid electrolyte layer 51 in reference gas chamber 15 opposite reference electrode 22. Measuring electrode 21 and reference electrodes 22, 22a form a concentration cell.

A barrier layer 24 is provided in the layer level between first and second solid electrode layers 51, 52 in the region of further reference electrode 22a and in the region between further reference electrode 22a and first pump electrode 20. Barrier layer 24 extends up to the edge of sensor element 10 and is made of, for example, $Al_2O_3$. The material of barrier layer 24 is selected in this case in such a way that it, at least to a large extent, allows neither ionic conduction nor electron conduction.

In a further embodiment of the present invention, not shown, barrier layer 24 also extends into the region between supply lead 28 of further reference electrode 22a and first solid electrolyte layer 51. It is also conceivable that the barrier layer covers the entire large area of sensor element 10 in the layer level between first and second solid electrolyte layer 51, 52, with a cutout being provided in the region of first pump electrode 20.

A further embodiment of the present invention, not shown, is conceivable in which further reference electrode 22a is dispensed with. In this case, barrier layer 24 can also be located in the layer level between second and third solid electrolyte layer 52, 53, particularly between partition wall 12 and third solid electrolyte layer 53.

What is claimed is:

1. A sensor element for determining a concentration of a gas component in a gas mixture, comprising:

a measuring gas chamber;

at least one pump cell including at least one first pump electrode situated in the measuring gas chamber and at least one second pump electrode situated on a surface of the sensor element facing the gas mixture;

a first solid electrolyte layer situated between the first and second pump electrodes;

a reference gas chamber;

at least one concentration cell including at least one reference electrode situated in the reference gas chamber and at least one measuring electrode cooperating with the reference electrode and being situated in the measuring gas chamber;

a second solid electrolyte layer adjacent to the first solid electrolyte layer, in which the reference gas chamber and the measuring gas chamber are situated;

at least one barrier layer substantially preventing ionic conduction between at least one of the electrodes of the pump cell and at least one of the electrodes of the concentration cell;

a layer level between the first and second solid electrolyte layers, the barrier layer being situated in regions in the layer level, the barrier layer having a cutout in a region of the first pump electrode; and a further reference electrode lying opposite the reference electrode in a reference gas channel, the barrier layer separating the reference electrode from the first solid electrolyte layer.

2. The sensor element according to claim 1, wherein the sensor element is for determining an oxygen concentration in an exhaust gas of an internal combustion engine.

3. The sensor element according to claim 1, wherein the barrier layer substantially prevents ionic conduction between the reference electrode and the second pump electrode.

4. The sensor element according to claim 1, wherein the barrier layer is situated in regions in a layer level of the sensor element between the reference electrode and the second pump electrode.

5. The sensor element according to claim 1, wherein the barrier layer has a cutout around the measuring electrode.

6. The sensor element according to claim 1, wherein the reference gas chamber is connected to a reference gas reservoir laying outside the sensor element, with the surrounding air.

7. The sensor element according to claim 1, wherein the barrier layer is situated between a supply lead of the further reference electrode and the first solid electrolyte layer.

8. The sensor element according to claim 1, further comprising a third solid electrolyte layer, the barrier layer being situated in regions between the first and third solid electrolyte layers, the barrier layer having a cutout in a region of the measuring electrode and the reference electrode.

9. The sensor element according to claim 8, wherein the barrier layer is situated between a supply lead of the reference electrode and the third solid electrolyte layer.

* * * * *